United States Patent
Kalb et al.

(10) Patent No.: US 6,432,447 B2
(45) Date of Patent: Aug. 13, 2002

(54) ORGANIC COMPOUNDS

(75) Inventors: Oskar Michael Kalb, Loerrach (DE); Stephen John Valazza, Matawan, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/859,861

(22) Filed: May 17, 2001

Related U.S. Application Data

(63) Continuation of application No. 09/549,222, filed on Apr. 13, 2000, now Pat. No. 6,242,003.

(51) Int. Cl.[7] .............................. A61K 9/22; A61K 9/20; A61K 9/28; A61K 9/36

(52) U.S. Cl. ....................... 424/468; 424/465; 424/474; 424/464; 424/480

(58) Field of Search .................................. 424/480, 468, 424/464, 465, 489, 482, 494, 473, 474; 514/451

(56) References Cited

U.S. PATENT DOCUMENTS

| | | | |
|---|---|---|---|
| 3,852,421 A | 12/1974 | Koyanagi et al. | 424/94 |
| 3,865,935 A | 2/1975 | Amann | 424/181 |
| 3,870,790 A | 3/1975 | Lowey et al. | 424/19 |
| 3,891,755 A | 6/1975 | Mehta | 424/157 |
| 3,952,096 A | 4/1976 | Godfrey | 424/156 |
| 4,226,849 A | 10/1980 | Schor | 424/19 |
| 4,259,314 A | 3/1981 | Lowey | 424/19 |
| 4,342,767 A | 8/1982 | Alberts-Schonberg et al. | 424/250 |
| 4,357,469 A | 11/1982 | Schor | 536/91 |
| 4,369,172 A | 1/1983 | Schor et al. | 424/19 |
| 4,389,393 A | 6/1983 | Schor et al. | 424/19 |
| 4,556,678 A | 12/1985 | Hsiao | 514/652 |
| 4,686,237 A | 8/1987 | Anderson | 514/532 |
| 4,744,987 A | 5/1988 | Mehra et al. | 424/156 |
| 4,755,385 A | 7/1988 | Etienne et al. | 424/154 |
| 4,755,386 A | 7/1988 | Hsiao et al. | 424/435 |
| 4,786,505 A | 11/1988 | Lovgren et al. | 424/468 |
| 4,853,230 A | 8/1989 | Lovgren et al. | 424/466 |
| 4,871,548 A | 10/1989 | Edgren et al. | 424/488 |
| 4,915,954 A | 4/1990 | Ayer et al. | 424/473 |
| 4,929,605 A | 5/1990 | Domet et al. | 514/54 |
| 4,997,658 A | 3/1991 | Alberts et al. | 424/473 |
| 5,004,651 A | 4/1991 | Becker | 424/465 |
| 5,009,895 A | 4/1991 | Chung | 424/465 |
| 5,030,447 A | 7/1991 | Joshi et al. | 424/80 |
| 5,045,321 A | 9/1991 | Makino et al. | 424/475 |
| 5,053,032 A | 10/1991 | Barclay | 604/892.1 |
| 5,126,145 A | 6/1992 | Evenstad et al. | 424/465 |
| 5,147,654 A | 9/1992 | Place | 424/473 |
| 5,284,662 A | 2/1994 | Koparkar et al. | 424/473 |
| 5,356,896 A | 10/1994 | Kabadi et al. | 514/256 |
| 5,376,383 A | 12/1994 | Alberts et al. | 424/478 |
| 5,393,765 A | 2/1995 | Infield et al. | 514/365 |
| 5,419,917 A | 5/1995 | Chen et al. | 429/469 |
| 5,624,677 A | 4/1997 | El Rashidy et al. | 424/435 |
| 5,674,893 A | * 10/1997 | Behounek et al. | 514/451 |
| 5,837,379 A | * 11/1998 | Chen et al. | 424/465 |
| 5,972,389 A | 10/1999 | Shell et al. | 424/501 |

FOREIGN PATENT DOCUMENTS

| | | |
|---|---|---|
| CA | 1285483 | 7/1991 |
| EP | 0 114 027 | 7/1984 |
| EP | 0 336 298 | 10/1989 |
| EP | 0 375 156 | 6/1990 |
| EP | 0 377 518 | 7/1990 |
| EP | 0 401 705 | 12/1990 |
| EP | 0 465096 | 1/1992 |
| EP | 0 487 774 | 6/1992 |
| EP | 0 547 000 | 6/1993 |
| EP | 0 609 961 | 8/1994 |
| EP | 0 413 061 | 1/1995 |
| EP | 0 662 322 | 7/1995 |
| GB | 2 195 893 | 4/1998 |
| JP | 10226644 | 8/1998 |
| WO | WO 87/00044 | 1/1987 |
| WO | WO 87/06130 | 10/1987 |
| WO | WO 93/18755 | 9/1993 |
| WO | WO 96/12478 | 5/1996 |
| WO | WO 96/19201 | 6/1996 |
| WO | WO 96/41619 | 12/1996 |
| WO | WO 97/23200 | 7/1997 |
| WO | WO 97/47285 | 12/1997 |
| WO | WO 97/49681 | 12/1997 |
| WO | WO 98/11879 | 3/1998 |
| WO | WO/98/15264 | 4/1998 |
| WO | WO 98/15290 | 4/1998 |
| WO | WO 98/41194 | 9/1998 |
| WO | WO 99/03453 | 1/1999 |

OTHER PUBLICATIONS

CA 114 (6) 49589K, Dennick, 1990.
Derwent Abstract 89–217777/30, I. Yoshimutsu, Slowly Releasing Drug Preparation, JP 01156909, Jun. 20, 1989.
Derwent Abstract 94–238639/29, M. Naoaki et al., Sustained Release Tablet, JP 06172161–A, Jun. 21, 1994.
Derwent Abstract 95–019192/03 M. Naosuke et al., Depot Tablet, JP 06305982–A, Apr. 28, 1993.
Derwent Abstract 90–135661/18 K. Hiroyasu et al., Sustained Release Tablet, JP 0 2083–316–A, Mar. 23, 1990.
Derwent Abstract 90–047900/07 N. Hiroaki, et al., Sustained Release Tablet, JP 0 2000–105–A, Jan. 5, 1990.
Derwent Abstract 82–73233, N. Tsuneji et al., Gradually Releasing Preparation, JP 57118511, Sep. 8, 1977.
International Search Report for International Application No. PCT/EP 99/07627.

* cited by examiner

*Primary Examiner*—Thurman K. Page
*Assistant Examiner*—Blessing Fubara
(74) *Attorney, Agent, or Firm*—John D. Thallemer

(57) ABSTRACT

An oral dosage form comprising fluvastatin and HPMC, which oral dosage form is color-stable upon prolonged periods of storage.

6 Claims, No Drawings

ORGANIC COMPOUNDS

This application is a continuation of application Ser. No. 09/549,222, filed Apr. 13, 2000 now U.S. Pat. No. 6,242,003, which in its entirety is herein incorporated by reference.

This invention is concerned with formulations for sustained release of fluvastatin.

Fluvastatin is a member of a class of drugs commonly referred to as HMG CoA reductase inhibitors (sometimes called "statins"). The statins are used to reduce blood cholesterol levels in patients in need of such treatment. The site of action of the statins is the liver. Conventional rapid release forms of statins, e.g. which release the statin within about 2 hours have mild side effects associated with systemic delivery of the statin. The statins appear to enter systemic circulation because of the relatively high concentration of statin entering the liver in a relatively short space of time tends to flood the liver such that some of the statin is not metabolised on the first pass.

Sustained release formulations have been suggested as a means of preventing or amelioratiing the side effects associated with systemic entry of the statins-lovastatin, simvastatin and pravastatin (see EP 0 375 156).

Several methods of providing sustained release formulations have been proposed in the art. One such means is to use certain excipients in a matrix which modify the release of an active agent dispersed within said matrix. Hydroxypropyl methyl cellulose (HPMC) polymers have been suggested as release-modifying excipients, either alone or in combination with other materials, in sustained release formulations for use with a wide variety of active agents including the HMG CoA reductase inhibitors, see for example U.S. Pat. No. 4,369,172, U.S. Pat. No. 4,357,469, U.S. Pat. No. 4,226,849 and U.S. Pat. No. 4,389,393. It is thought that formulations containing HPMC polymers prolong drug release by forming a gelatinous matrix upon exposure to the aqueous medium of the stomach which prevents or delays ingress of the aqueous medium of the stomach into the dosage form and thereby preventing its rapid disintegration. The gel matrix is thought to form as a result of hydration of the HPMC polymer. However, the applicant could not find any suggestion that hydration of the HPMC occurred during storage of oral dosage forms containing HPMC Furthermore, whether hydration occurs during storage or not, none of the aforementioned documents refer to any instability problems associated with the use of HPMC and in particular colour instability.

The applicant was therefore surprised to find that dosage forms comprising HPMC polymers formed gel-like domains upon storage, which domains, still more surprisingly were highly coloured. Whereas this discolouration left the dosage forms with an unsightly, uneven mottled appearance, it was of no consequence for the safety and efficacy of the dosage forms. Nevertheless, the mottled appearance may by disturbing to patients and lead to poor patient compliance.

There is a need, therefore to provide dosage forms of fluvastatin for sustained release which are colour-stable upon prolonged periods of storage.

In accordance with the present invention there is provided oral dosage forms comprising a mixture of fluvastatin, HPMC polymers and optionally other pharmaceutical excipients which are colour-stable upon prolonged periods of storage.

As used hereinbove, "colour-stable" used in connection with oral dosage forms is taken to mean said dosage form in which the mottled disclouration hereinabove described is either substantially prevented or is present at levels not detectable by visual inspection, i.e. the mottled disclouration is either so faint as to be not apparent or it is capable of being masked by one or more excipients, e.g. colouring agents.

The presence of the gel-like domains may be detected by visual appearance alone. However, it may also be detected using known analytical techniques, for example microcalorimetry. Microcalorimetry may detect any heat flow, e.g. an exotherm as a result of excipient interactions, e.g. an exotherm associated with the hydration of HPMC. It is a characteristic of oral dosage forms of the invention that they display a significant heat flow, i.e. a heat flow of greater than 5 micro Watts, e.g. up to 59 micro Watts, more particularly 19 to 59 micro Watts over a relatively long period of time, e.g. a period of 48 hours, when subjected to a stress test at 40 degrees centigrade and 75% relative humidity. The stress test may be carried out on an isothermal microcalorimeter (CSC Corporation, Provo. Utah) set to 40 degrees centigrade. The oral dosage form may be subjected to an environment of 75% relative humidity by, e.g. by preparing minihydrostats using a sodium chloride solution inside 250 microlitre polypropylene vial inserts.

As stated hereinabove, colour-stability may be achieved by substantially preventing or modulating the formation of HPMC gels. One means of achieving the object of colour stability may be to reduce the ambient moisture levels surrounding the oral dosage forms during storage. Applicant has found that oral dosage forms stored under conditions such that the relative humidity does not exceed 75%, more preferably no more than 60%, e.g. 40 to 60% at a temperature of between 25 and 40 degrees centigrade, display a markedly reduced tendency towards discolouration. The type of packaging employed may also reduce discolouration. Whereas conventional blister packaging may be employed, e.g. Triplex TPX blisters, it is preferred to use high density polyethylene (HDPE) bottles. Oral dosage forms as hereinabove described packaged in HDPE bottles may exhibit substantially no discolouration associated with the formation of HPMC gels. Oral dosage forms as hereinabove described packaged in HDPE bottles form another aspect of the present invention.

Oral dosage forms according to the invention may be formulated in any conventional form, e.g. powders, capsules or tablets. Preferred oral dosage forms may be in the form of tablets.

Oral dosage forms hereinabove described may be formed of a granulated mass comprising fluvastatin, HPMC and optionally other excipients commonly used in oral dosage forms, e.g. tablets. Surprisingly the applicant has found that the finer is the mean particle size of the granulated mass the less intense is the observed mottled disclouration. The applicant believes that the increased colour stability observed as the mean particle size is decreased may be due to the ability of the finer granules to form a tighter compact when compressed, thereby reducing the incidence and size of any voids in the compacted mass. As the HPMC gels are thought to form in these voids, the smaller their number and/or size, the less tendency there is for gels to form.

Preferred oral dosage forms are tablets which are formed of granulates having a mean granulate particle size of less than about 200 microns, e.g. less than 125 microns, more particularly 100 to 125 microns. However, the contribution to the art is the recognition of a correlation between granulate size and the incidence and nature of the disclouration. It follows that the skilled artisan will understand that for different excipient mixtures, e.g. amounts of HPMC polymer, the incidence and nature of discolouration may vary within this preferred range, and in fact discolouration may be absent or visually insignificant outside of the aforementioned ranges. However, with no more than routine experimentation, the skilled person will be able to determine a suitable granulate size for a given excipient mixture. Granulates as hereinabove described and oral dosage forms, e.g. tablets made therefrom are further aspects of the present invention.

The reduction of moisture levels surrounding the oral dosage forms upon storage and the use of fine granulates as hereinabove described may be used alone or in combination to achieve the objects of the present invention.

As is clear from the definition provided above, an oral dosage form may be "colour-stable" notwithstanding that it may contain significant amounts of HPMC gel such that the mottled discolouration would be quite apparent were it not for the presence of a colouring agent masking said discolouration.

Accordingly the invention provides in another of its aspects an oral dosage form comprising a core containing fluvastatin, HPMC and optionally other excipients, wherein the core contains domains of HPMC gel, and a colouring agent provided in sufficient amounts to mask any mottled discolouration associated with the HPMC gel domains.

Fluvastatin is known to exhibit a tendency towards photodegradation to give a highly coloured degradation product. Whereas this degradation is slight and has no consequence on the efficacy and safety of dosage forms containing fluvastatin, it is preferred to employ a colouring agent to mask any discolouration associated with this photodegradation. However, as fluvastatin is typically dispersed essentially uniformly about oral dosage forms any discolouration of this type tends to be rather subtle and uniform. This subtle, dispersed discolouration may therefore be masked simply by using conventional colouring agents in relatively low amounts. This is fortunate, as the amounts of colouring agent, e.g. Iron oxides, that may be employed in pharmaceutical formulations are strictly controlled by regulatory authorities. For example in the case of iron oxide pigments, the amount of elemental iron acceptable for ingestion is currently set at 5 mg/day by the FDA.

However, in contrast to the discolouration associated with the photodegradation of fluvastatin, the discolouration associated with the formation of the HPMC gel tends to occur in discrete, random domains. The discolouration tends therefore to be more concentrated and therefore more intense, and patchy and as such is more difficult to mask. As such, conventional colouring agents employed in relatively small amounts do not provide adequate coverage.

The applicant was therefore faced with the problem of how to mask the unsightly, mottled appearance yet at the same time keeping the amount colouring agent, in particular iron-containing colouring material as small as possible.

Accordingly, the invention provides in another of its aspects an oral dosage form comprising a core comprising a pharmaceutically active agent, HPMC and optionally other excipients, and a coating wherein said coating comprises a colouring agent present in sufficient amounts to mask any mottled discolouration associated with the formation of HPMC gel.

Whereas the preceding paragraph provides that the colouring agent is contained in the coating. However, it is within the scope of the present invention that the colouring agent may be employed in admixture with the active agent and other excipients in the core. In such an embodiment a coating would be optional The colouring agent may be selected from any of those colouring agents known in the art, for example pigments, in particular any of the colouring agents known for use in pharmaceutical preparations are suitable for use in the present invention, see for example "Handbook of Pharmaceutical Excipients, 2nd Edition (1994), Eds. Wade and Weller", at pages 130–134. Suitable colouring agents include titanium dioxide, iron oxide (both ferrous and ferric), preferably $Fe_2O_3$ optionally in hydrated form. In a most preferred embodiment a combination of colouring agents may be used e.g., titanium dioxide and iron (II) oxide.

Having regard to the amount of colouring agent that may be employed in a unit dosage form, the maximum amount will be subject to the maximum daily limits of the given colouring agent permitted by regulatory authorities, and may vary below this limit according to the number of unit dosage forms to be taken per day, e.g. whether the oral dosage form is once- or twice-a-day, and the size of a given unit dosage form. With these considerations in mind, the skilled artisan would be able to determine an appropriate amount of colouring agent to effectively mask any mottled discolouration without undue burden.

In a preferred embodiment the colouring agent may constitute up to 73% by weight based on the total weight of the coating, more particularly 17 to 30%, e.g. 22 to 25%. The percentages referred to represent the total colouring agent employed. i.e. the total colouring agent may be made composed of one colouring agent, e.g. iron (II) oxide, or a combination, e.g. titanium dioxide and iron (II) oxide.

Suitable coating materials include those materials conventionally used in coating tablets, granules and the like. Preferred coating materials are hydrophilic and permeable to, and/or at least to some extent soluble in, water and intestinal fluids. Any of the coating materials, in particular the elastic coatings described in the art are suitable for the purposes of the present invention.

Coating materials as hereinabove defined may be used in admixture with other excipients, conventional in coating formulations, for example talcum or silicon dioxide, for example synthetic amorphous silicic acid of the Syloid® type (Grace), for example SYLOID 244 FP, or wetting agents, for example the afore-mentioned polyethylene glycols or sorbates.

The coating materials may comprise additional excipients, for example plasticisers e.g. triethyl citrate, e.g. Citroflex® (Pfizer), triacetin, various phthalates, e.g. diethyl or dibutyl phthalate, mixed mono- or di-glycerides of the Myvacet® type (Eastman), for example MYVACET 9-40, the polyethylene glycols mentioned hereinbefore, for example having a molecular weight of approximately from 6000 to 8000, and also ethylene oxide/propylene oxide block copolymers of the Pluronic® (BASF) or Synperonic® (ICI) type, pulverulent mould release agents, for example magnesium trisilicate, starch or synthetic amorphous silicic acid of the SYLOID type, for example SYLOID 244 FP.

Coating weights employed in oral dosage forms according to the invention may vary within limits conventional in the art, and typically may be in the range of about 1 to about 4% by weight based on the total weight of the formulation, for example about 3% by weight.

In particularly preferred embodiments, for a 20 mg coated tablet the coat weight is about 2 to 2.5 mg, e.g. 2.44 mg; for a 40 mg coated tablet the coat weight is about 4.5 to 5.0 mg, e.g 4.86 mg; for 80 mg coated tablets the coat weight is 9.5 to 10.0 mg, e.g. 9.75 mg; and for 160 mg coated tablets the coat weight is about 12.0 to 12.5 mg, e.g. 12.3 mg.

Oral dosage forms according to the invention comprise any of the commercially available hydroxypropylmethyl cellulose polymers that are suitable for the purpose of providing for sustained release of the active agent and include any of those materials referred to in EP 375156, U.S. Pat. No. 4,369,172, U.S. Pat. No. 4,357,469, U.S. Pat. No. 4,226,849 and U.S. Pat. No. 4,389,393 which are incorporated herein by reference.

A preferred HPMC polymer is available from Dow Corning under the trade name METHOCEL. Preferably the HPMC will have a hydroxypropyl (HP) degree of substitution of up to about 12, i.e. the HPMC will comprise up to about 12 percent HP functionality. More preferably the HPMC will have HP functionality of from 7 to 12 percent, most preferably 7 to 9 percent. The HPMC may have normal viscosity (2.0% HPMC in water) of from about 100 to 100,000 centipoise and a number average molecular weight of about 20,000 to about 170,000. A particularly preferred HPMC is METHOCEL K100LV, which has a number average molecular weight of about 20,000 to about 30,000. Methods of making such HPMC polymers are well known in the art.

HPMC polymers may be employed in amounts sufficient to ensure sustained release of the fluvastatin. By "sustained release" is meant that the fluvastatin is released from the oral dosage form over an extended period of time, e.g. greater than about 6 hours. In a preferred oral dosage form the less than about 80% by weight of the fluvastatin is released in the first 8 hours after ingestion of the oral dosage form, with the remaining fluvastatin being release thereafter. In more preferred compositions, less than about 15% by weight of the fluvastatin is release after 0.5 hour after ingestion, form about 10 to 50% by weight is released within 2 hours after ingestion, and about 40 to 60% is released after 6 hours. Preferably oral dosage forms according to the invention comprise about 15 to about 50% by weight of HPMC, more preferably about 20 to 40%. The HPMC and a non-ionic hydrophilic polymer (discussed hereinbelow) preferably are present in a weight ratio of HPMC: non-ionic polymer of about 10:1 to about 3:1, more preferably 7:1 to 5:1, most preferably 6:1.

Whereas HPMC is a useful excipient to ensure sustained release of fluvastatin from an oral dosage form, applicant has found that conventional sustained release formulations containing HPMC alone as the rate-modifying excipient may nevertheless exhibit an initial drug burst or premature release of fluvastatin. By "premature release" is meant that a substantial amount of fluvastatin may be released in a short period of time after ingestio[008e] such that the amount of active agent delivered to the site of action is above the therapeutic level. Whereas this may not have any consequence for the efficacy of the drug substance there may be resultant toxic side effects associated with the greater than therapeutic dose. Surprisingly the applicant has discovered that the premature release may be avoided or ameliorated if the oral dosage form additionally comprises at least one non-ionic hydrophilic polymer.

Non-ionic hydrophilic polymers used in oral dosage forms according to the invention may be selected from the group consisting of hydroxyethylcellulose (HEC) having a number average molecular weight of from 90,000 to 1,300,000, preferably about 1,000,000 to about 1,300,000; hydroxypropyl cellulose (HPC) having a number average molecular weight of 370,000 to 1,500,000, preferably 850,000 to 1,500,000, more preferably 1,000,000 to 1,200,000 and poly(ethylene)oxide (PEO) having a number average molecular weight of about 100,000 to 500,000, preferably 150,000 to 300,000, more preferably 200,000.

Examples of HEC polymers are commercially available from Hercules Incorporated, Aqualon Division under the tradename NATROSOL 250H or NATROSOL 250L. Examples of HPC polymers are also available from Hercules Incorporation, Aqualon Division under the tradename KLUCEL or KLUCEL HXF, and examples of PEO polymers are available from Union Carbide Corporation under the tradename POLYOX. Methods of making the non-ionic hydrophilic polymers heretofore described are known to those skilled in the art. The non-ionic hydrophilic polymers may be employed in oral dosage forms according to the invention in amounts ranging from about 1 to about 20% by weight, preferably about 3 to 12% by weight, more preferably about 4 to 7% by weight based on the total weight of the oral dosage form. The non-ionic hydrophilic polymer is present in an amount sufficient to prevent premature release of fluvastatin.

Oral dosage forms according to the invention may comprise other excipients which serve to facilitate processing and/or provide enhanced properties of the oral dosage forms, including well known tabletting excipients such as binders, e.g gelatin, sugars, natural and synthetic gums, polyvinylpyrollidone), disintegrants (e.g. crosscarmelose, crospovidone, sodium starch glycolate), lubricants (e.g., magnesium stearate, hydrogenated vegetable oils, carnauba wax), flow agents (e.g. silicon dioxide), anti-adherents or glidants (e.g. talc) as well as sweeteners, fillers, flavourants and antioxidants.

As fluvastatin is sensitive to acidic media, it is conventional to include a basifying agent to impart a pH of at least about 9. Any basifying agent known for stabiliising formulations containing HMG CoA reductase inhibitors may be employed. Applicant has surprisingly found that in oral dosage forms comprising a typical basifying agent, e.g. potassium carbonate or bicarbonate, and polyvinylpyrollidone and fluvastatin, there is a tendency for discolouration during storage. This discolouration, in the form of dark spots, is distinct from that hereinabove described and is thought to be a result of the action of in situ -generated carbonic acid on the active agent or excipients (the carbonic acid being formed as a degradation product of the potassium carbonate or bicarbonate in the presence of PVP and ambient moisture). In keeping with the discolouration associated with the HPMC, this discolouration does not affect the safety and efficacy of the oral dosage forms and is likewise masked by adopting the same precautions as hereinabove described.

Whereas the oral dosage forms described hereinabove are used to administer fluvastatin, they may be employed to deliver other HMG CoA reductase inhibitors such as simvastatin, pravastatin, lovastatin, atorvastatin and cerivastatin. The HMG CoA reductase inhibitors may be used in their free-acid forms, their ester forms, e.g. lactone forms or as pharmaceutically acceptable salts, e.g sodium salts.

The structure and method of manufacture of fluvastatin is disclosed in European patent applications EP-A-114 027 and EP-A-547 000, which are incorporated herein by reference. Oral dosage forms according to the invention may be manufactured according to any of the procedures known in the art. In the case of tablets they may be formed by a process which forms another aspect of this invention and which comprises the step of an aqueous high-shear granulation of the active agent and the tabletting excipients.

Granules are produced in a manner known per se, for example using aqueous granulation methods known for the production of "built-up" granules or "broken-down" granules.

Methods for the formation of built-up granules operate continuously and comprise, for example, simultaneously spraying the granulation mass with granulation solution and drying, for example in a drum granulator, in pan granulators, on disc granulators, in a fluidised bed, by spray-drying or spray-solidifying, or operate discontinuously, for example in a fluidised bed, in a batch mixer or in a spray-drying drum.

Preferred are methods for the production of broken-down granules, which can be carried out discontinuously and in which the granulation mass first forms a wet aggregate with the granulation solution, which aggregate is then comminuted or formed into granules of the desired particle size using known granulation methods, the granules then being dried. Suitable granulators include, for example an Alexander granulator.

The granulation mass consists of comminuted, preferably ground, active ingredient and the excipients mentioned above. Depending on the method used, the granulation mass may be in the form of a premix or may be obtained by mixing the active ingredient into one or more excipients or mixing the excipients into the active ingredient. The wet granules are preferably dried, for example in the described manner by spray drying or in a fluidised bed.

Compression to form tablet cores may be carried out in conventional tabletting machines, for example EK-0 Korsch eccentric tabletting machines. The tablet cores may be of various shapes, for example round, oval, oblong, cylindrical etc., and various sizes, depending on the amount of active ingredient employed.

There now follows a series of example which serve to illustrate the invention.

EXAMPLE 1

A portion of fluvastatin sodium is calculated and weighed. Potassium bicarbonate, microcrystalline cellulose, povidone, HPC, and HPMC are weighed and placed into individual separately labelled containers. A 20 weight percent excess of the batch quantity of OPADRY Yellow, YS-1-6347-G, is then placed into a labelled container. The microcrystalline cellulose, fluvastatin sodium, povidone, HPC, and HPMC are transferred, in that order, into a collette gral and mixed for 5 minutes with the plow at slow speed and the chopper off. The resulting mixture is passed through a 0.033 inch screen using a tornado mill with knives forward and at a slow speed. The screened material is then mixed again in a collette gral with the plow at slow speed and the chopper off.

Potassium bicarbonate is dissolved into purified water until a clear homogenous solution is obtained. The potassium bicarbonate solution is then combined with the screened material, and the resulting mixture is granulated in a collette gral with the plow at fast speed and the chopper at slow speed. After adding the above solution, granulation should continue for 30 seconds with the plow at fast speed and the chopper at slow speed and for another 30 seconds with the plow at fast speed and the chopper at fast speed. The granulated mixture is then dried in a fluid bed dryer using a target inlet temperature of 50 degrees C until an LOD of 2 percent to 3 percent is obtained.

The dried granules are then passed through a 1/16 inch screen using a tornado mill with knives forward and at slow speed. An amount of magnesium stearate based on the proportion of actual yield from the 1/16 inch screening step to the theoretical yield from the same step is calculated and weighed. The weighed magnesium stearate is then passed through a 60 mesh screen and blended with the dried granules in a free fall blender and the resulting granulation blend discharged into a plastic lined labelled drum. The granulation blend is then compressed into tablets and the tablets are dedusted, passed through a metal checker, and stored in a plastic, labelled drum.

To coat the tablets, the OPADRY Yellow is mixed with a required quantity of purified water to obtain a 10 w/w percent suspension. The tablets are transferred to a coating pan and warmed to a temperature of 40–45 degrees C. The OPADRY Yellow suspension is then added, to spray coat the tablets until a 3 percent solid weight gain per tablet is achieved. The coating spray is shut off, and the tablets are cooled by shutting off the pan heat and jogging the pan for 5 minutes.

EXAMPLE 2

84.24 mg of fluvastatin sodium were combined with the following excipients according to the method described in Example 1 to provide a single dosage form described in Table 1:

TABLE 1

| | |
|---|---|
| Fluvastatin sodium | 84.24 mg |
| Potassium bicarbonate, USP | 8.42 mg |
| Microcrystalline cellulose, NF, PHI 0 1 (AVICEL). | 111.26 mg |
| Povidone USP | 4.88 mg |
| HPC, NF (KLUCEL HXF) | 16.25 mg |
| HPMC, USP (METHOCEL K 100 LV) | 97.50 mg |
| Magnesium Stearate | 2.44 mg |
| OPADRY Yellow | 9.75 mg |

The OPADRY yellow consisted of HPMC 2910 3 cps (72% ww); titanium dioxide (21.413% ww); PEG 8000 (4.0% ww); and iron oxide yellow (2.587% ww) (24% oxides $TiO_2+FeO_2$).

The formulation of Table 1 produced oral dosage forms which showed no sign of the mottled discolouration.

When the OPADRY yellow consisted of HPMC 2910 3 cps (80% ww); titanium dioxide (14.080% ww); PEG 8000 (4.0% ww); and iron oxide yellow (1.920% ww) (16% oxides $TiO_2+FeO_2$), the oral dosage forms displayed a mottled, uneven discolouration.

What is claimed is:

1. A colour-stable sustained release tablet comprising fluvastatin, a hydroxypropyl methyl cellulose polymer, and a coating material; wherein the coating material comprises a hydroxypropyl methyl cellulose polymer in an amount of less than or equal to 73 weight percent, and a colouring agent in an amount of from 18 to 30 weight percent, wherein the weight percents are based on the total weight of the coating material.

2. The tablet ac to claim 1 wherein the hydroxypropyl methyl cellulose polymer in the coating material comprises up to 12 percent hydroxypropylfunctionality and has a number average molecular weight of about 20,000 to about 170,000.

3. The tablet according to claim 2 wherein the hydroxypropyl methyl cellulose polymer has a viscosity of 100 to 100,000 centipoise as determined at a concentration of 2.0 weight percent of polymer in water.

4. The tablet according to claim 2 wherein the hydroxypropyl methyl cellulose polymer has a number average molecular weight of 20,000 to 30,000.

5. The tablet according to claim 1 wherein the colouring agent is present in an amount of 22 to 25 weight percent.

6. The tablet according to claim 1 wherein the colouring agent is a combination of titanium dioxide and iron (II) oxide.

* * * * *